United States Patent [19]

Chubachi et al.

[11] Patent Number: 4,459,852

[45] Date of Patent: Jul. 17, 1984

[54] ACOUSTIC MICROSCOPE USING LINE-FOCUS ACOUSTIC BEAM

[76] Inventors: Noriyoshi Chubachi, No. 4-6-203, 1-Chome; Junichi Kushibiki, No. 48, Aza-Nakazaike, Arai, Sendai City, both of Japan

[21] Appl. No.: 395,711

[22] Filed: Jul. 6, 1982

[30] Foreign Application Priority Data

Jul. 8, 1981 [JP] Japan .................................. 56-107402

[51] Int. Cl.$^3$ ............................................. G01N 29/00
[52] U.S. Cl. .......................................... 73/606; 73/642
[58] Field of Search .................................. 73/606, 642

[56] References Cited

U.S. PATENT DOCUMENTS

| | | | |
|---|---|---|---|
| 3,663,842 | 5/1972 | Miller ...................................... | 73/642 |
| 4,378,699 | 4/1983 | Wickramasinghe ................... | 73/606 |

OTHER PUBLICATIONS

"Linearly Focused Acoustic Beams for Acoustic Microscopy", Kushibiki et al, *Electronics Letters*, vol. 17, No. 15, Jul. 1981, pp. 520-522.

Applied Physics Letters, vol. 34, No. 3, Feb. 1, 1979 pp. 179-181.

IEEE 1981 Ultrasonics Symposium, pp. 552-556.

*Primary Examiner*—Howard A. Birmiel
*Attorney, Agent, or Firm*—Parkhurst & Oliff

[57] ABSTRACT

An acoustic microscope using a line-focus acoustic beam is disclosed. The line-focus acoustic beam is generated by an acoustic transducer head having an acoustic transducer electrode applied on a flat end surface of a sapphire rod, in the opposite end surface is formed a cylindrical concave surface. The acoustic transducer head is arranged fixedly above a mechanical stage on which a specimen is placed. The mechanical stage is movable in a Z axis, i.e. an axis of the line-focus acoustic beam and is also rotatable about the Z axis. By moving the stage in the Z-axis, a V(z) curve is obtained and a phase velocity of a leaky surface-acoustic wave is calculated from a repetition period of the V(z) curve. Then the V(z) curve measurement is repeated while the stage is rotated, and it is possible to obtain anisotropies of the specimen expressed by a relation between the rotational angle and the phase velocity of the leaky surface-acoustic wave.

14 Claims, 21 Drawing Figures

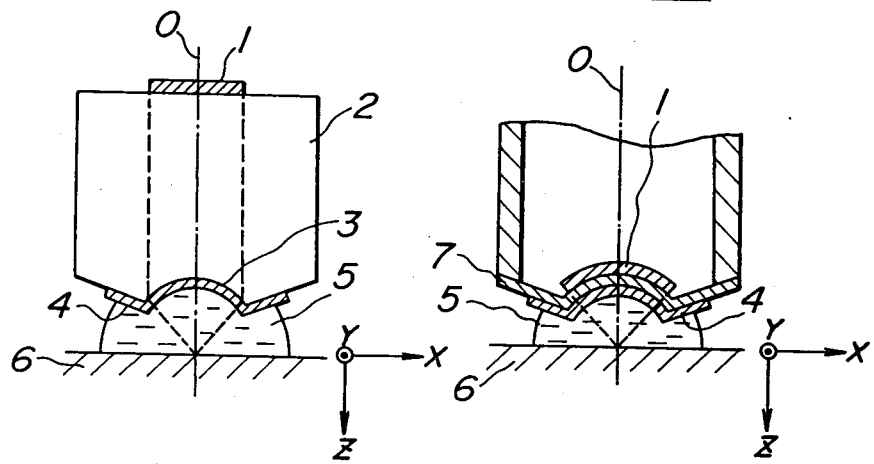
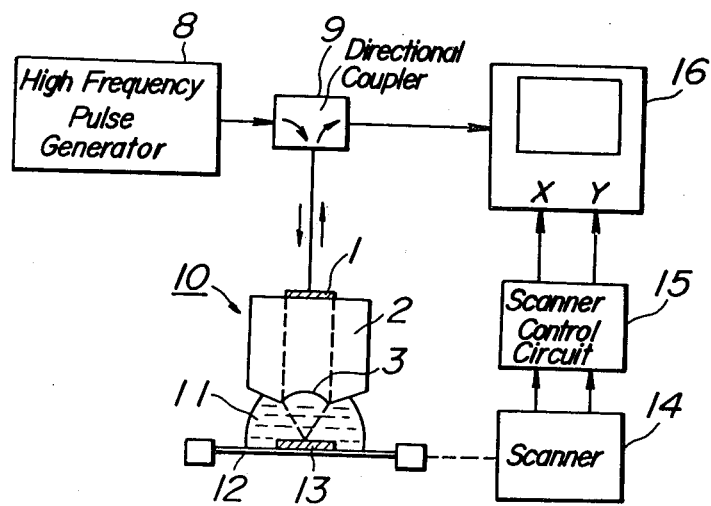

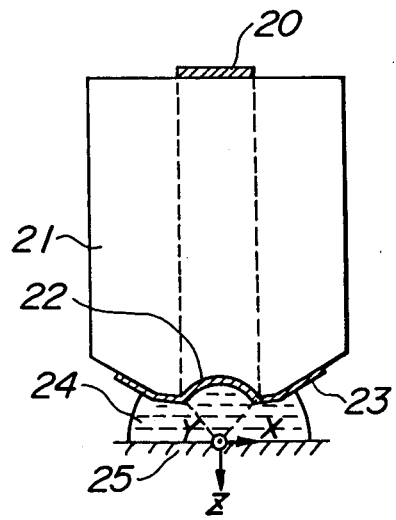
FIG_4a
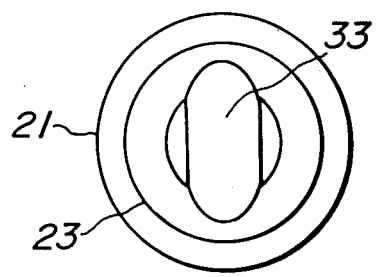
FIG_4b

FIG_5a
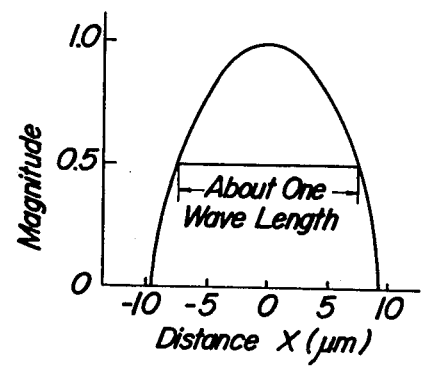
FIG_5b
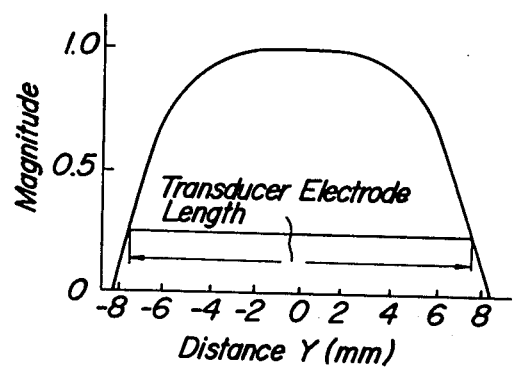

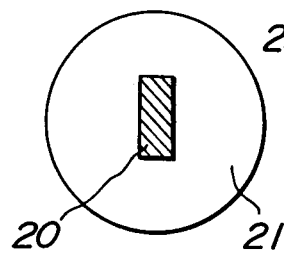
FIG._8a
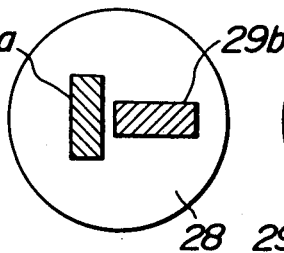
FIG._8b
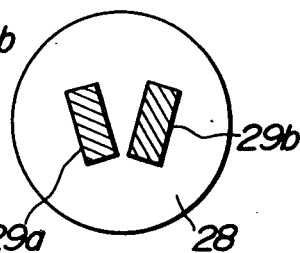
FIG._8c
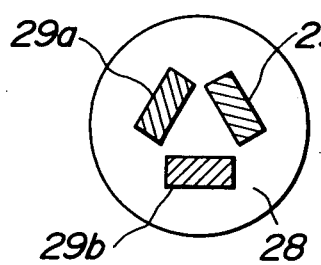
FIG._8d
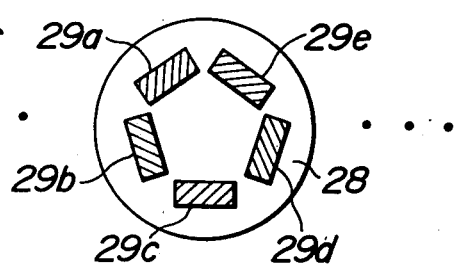
FIG._8e
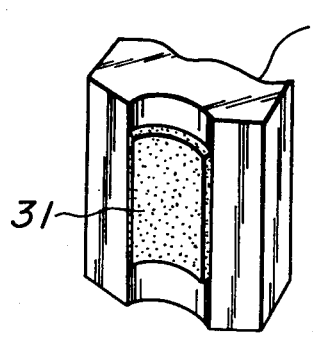
FIG._9a
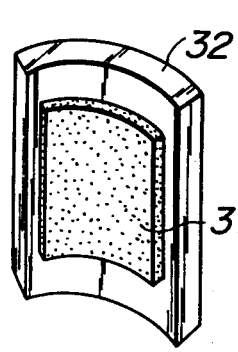
FIG._9b
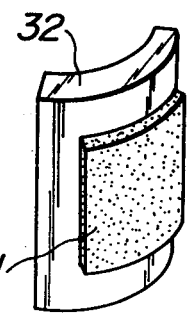
FIG._9c

ACOUSTIC MICROSCOPE USING LINE-FOCUS ACOUSTIC BEAM

BACKGROUND OF THE INVENTION

The present invention relates to an acoustic microscope comprising an electroacoustic transducer head for converting an electric signal into a focused acoustic beam emitted toward a specimen whose acoustic properties are to be measured and for reconverting acoustic energy reflected by or transmitted through the specimen into an electrical signal.

It has been known for a long time to investigate or study microscopic structures of materials with the aid of acoustic wave, i.e. ultrasonic beam instead of a radiation beam. Recently, a mechanically scanned acoustic microscope has been developed and in which a conically focused acoustic beam is projected upon a specimen to be analyzed and a focal point is moved in a plane of specimen or in a vertical direction perpendicular to the plane of specimen. Then, acoustic waves reflected by or transmitted through the specimen mainly due to difference in elastic property at specimen various points of the specimen are collected by an acoustic transducer head to be converted into an electrical signal. This electrical signal is then displayed two-dimensionally on a dispaly screen of a cathode ray tube to obtain a microscopic image of the specimen or is recorded by means of an X-Y recorder. The acoustic microscope may be classified into a transmission type and a reflection type depending upon an arrangement of the acoustic transducer head.

FIGS. 1a and 1b show schematically two examples of the known acoustic transducer head for emitting the conically focused acoustic beam. FIG. 1a illustrates an acoustic lens type transducer head and FIG. 1b shows a concave transducer type one, and both transducer heads are constructed symmetrically about a center line 0. In the acoustic lens type transducer head shown in FIG. 1a, an acoustic transducer element 1 made of piezoelectric material emits acoustic plane waves into a solid state acoustic field medium 2 and the thus emitted waves are propagated therethrough. The acoustic plane waves thus propagated are focused into a conical acoustic beam by means of an acoustic lens composed of an optically polished semispherical concave surface 3 and an anti-reflection coating 4 having a quarter wavelength. The conically focused acoustic beam is transmitted through a liquid state acoustic field medium 5 and is projected upon a specimen or sample 6 to be studied.

In the concave transducer type acoustic microscope illustrated in FIG. 1b on a metal plate 7 having a semispherical concave surface formed therein is applied an anti-reflection coating 4 of a quarter wavelength and an acoustic transducer element 1 made of piezoelectric material is applied on a convex surface of the metal plate 7. In this case, a conically focused acoustic beam of aberration free is projected via a liquid state acoustic field medium 5 onto a specimen 6.

FIG. 2 is a block diagram illustrating a whole construction of a reflection type acoustic microscope comprising the acoustic transducer head 10 shown in FIG. 1a. A signal generated from a high frequency pulse generator 8 is supplied via a directional coupler 9 to the acoustic transducer head 10 which then projects a conically focused acoustic beam through a liquid state acoustic field medium 11 upon a specimen 13 placed on a mechanical stage 12. A position of the mechanical stage 12 in a Z axis is so adjusted that the specimen 13 is placed in a vicinity of a focal point ($Z \cong 0$) and then the stage 12 is moved in X and Y axis directions by means of a scanner 14. It should be noted that the acoustic transducer head 10 may be moved in the X and Y directions. The scanner 14 is controlled by a scanner control circuit 15. Acoustic waves reflected by the specimen 13 are collected by the acoustic transducer head 10 and are converted into an electrical signal which is then supplied via the directional coupler 9 to a display device 16 which is synchronously driven by the scanner control circuit 15 to display an acoustic microscopic image of the specimen 13.

FIG. 3a is a block diagram illustrating another example of the known acoustic microscope in which a specimen 13 is placed on a mechanical stage 17 which is moved in the Z axis direction under the control of a stage control circuit 18. When an output electrical signal obtained from a directional coupler 9 is recorded by a recorder 19, while the specimen 13 is moved toward the acoustic transducer head 10, there is obtained a curve as shown in FIG. 3b which is usually called a V(Z) curve and its periodicity, i.e. an interval between dips is dependent upon acoustic property of the specimen 13. It has been experimentally confirmed that these periodic dips are caused by interference between acoustic waves near the Z axis directly reflected from the sample and those reradiated from the sample via a leaky surface-acoustic wave excited by the beam near a critical angle $\theta_l$. In other words, the period $\Delta Z$ of the V(Z) curve is strongly related to the phase velocity of the leaky surface-acoustic wave. Therefore, by measuring a period $\Delta Z$ of the V(Z) curve in FIG. 3b, the velocity of the leaky surface-acoustic wave may be calculated. The period $\Delta Z$ and velocity Vs may be given approximately by the following equations.

$$\Delta Z = V_l / \{2f(1 - \cos \theta_l)\} \tag{1}$$

$$\theta_l = \sin^{-1}(V_l/V_s) \tag{2}$$

Here, $V_l$ is a velocity of the longitudinal wave in the liquid state acoustic propagating medium 11, Vs is the velocity of the leaky surface-acoustic wave and f is an acoustic frequency. From the above equations it is apparent that the velocity $V_s$ of the leaky surface-acoustic wave in the solid state material can be calculated from the measured value of $\Delta Z$ in accordance with the following equation.

$$V_s = V_l / \{1 - (1 - V_l/2f\Delta Z)^2\}^{\frac{1}{2}} \tag{3}$$

An example of such a measurement is described in "A model for predicting acoustic material signatures", APPLIED PHYSICS LETTERS, Vol. 34, No. 3, Feb. 1, 1979, written by R. D. Weglein. In this paper, many samples were measured with wide velocity ranges and it has been demonstrated experimentally that the period $\Delta Z$ is strongly related to the phase velocity of the leaky surface-acoustic wave and thus, the measured results can provide useful information for quantitative analysis of acoustic properties of solid state materials.

In the known method for measuring the velocity of acoustic wave, use is made of the conically focussed beam both in the acoustic lens type and the concave surface transducer type. The acoustic beam is focused two-dimensionally and has a beam waist of about one wavelength. This acoustic beam is composed of components in all directions about the Z-axis, i.e. beam axis and thus, the acoustic properties are measured as a mean value around the beam axis. In other words, even if the specimen has anisotropies about the Z-axis, the measured value does not reflect such anisotropies. The inventors have found out that much more useful information about acoustic properties of materials can be obtained by detecting anisotropies of materials as a function of angle around the beam axis normal to the specimen through the V(Z) curve measurements.

SUMMARY OF THE INVENTION

The present invention has for its object to provide a novel and useful acoustic microscope which can measure V(Z) curves for the leaky surface-acoustic wave propagating in any given direction.

It is another object of the invention to provide an acoustic microscope which can provide acoustic anisotropies of materials as a function of angle around an acoustic beam axis through the V(Z) curve measurement.

According to the invention, an acoustic microscope for detecting acoustic properties of a specimen comprises an acoustic transducer head for emitting toward the specimen an acoustic beam which is linearly focussed along one direction perpendicular to the direction of propagation of the acoustic beam.

In a preferred embodiment of the acoustic microscope according to the invention, the acoustic microscope further comprises means for moving relatively the acoustic transducer head and the specimen in the direction of acoustic beam propagation, and means for rotating relatively the acoustic transducer head and the specimen about an axis parallel to the direction of propagation of the acoustic beam.

BRIEF DESCRIPTION OF THE DRAWINGS

FIGS. 1a and 1b are cross sections showing two examples of a known acoustic transducer head for producing a conically focused acoustic beam;

FIG. 2 is a block diagram illustrating a whole construction of a known acoustic microscope utilizing the acoustic transducer head shown in FIG. 1a;

FIGS. 4a and 4b are cross sectional and bottom views, respectively showing an embodiment of an acoustic transducer head according to the invention;

FIGS. 5a and 5b are graphs illustrating distribution curves of acoustic field of a linearly focused acoustic beam emitted from the acoustic transducer head shown in FIGS. 4a and 4b;

FIGS. 8a to 8e are schematic plan views illustrating various embodiments of the acoustic transducer head according to the invention; and FIGS. 9a to 9c are perspective views showing other embodiments of the acoustic transducer head according to the invention.

DESCRIPTION OF THE PREFERRED EMBODIMENTS

Figure 3A:
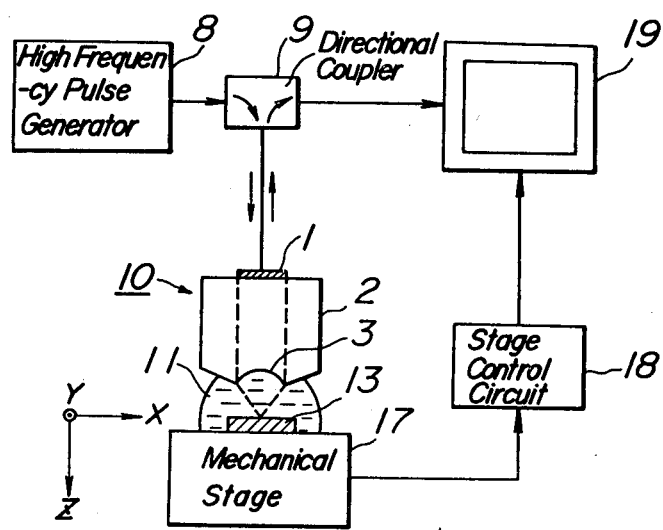
FIG. 3a is a block diagram depicting a whole construction of another known acoustic microscope for measuring a V(Z) curve and FIG. 3b is a graph showing a typical V(Z) curve.
Figure 3B:
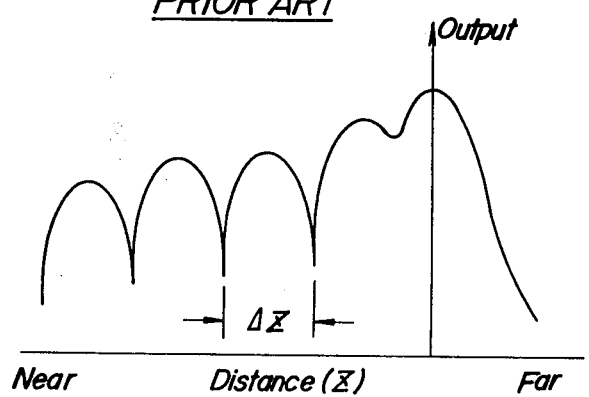

FIGS. 4a and 4b are cross sectional and bottom views showing an embodiment of an acoustic transducer head according to the invention. The acoustic transducer head of the present embodiment is of the acoustic lens type. An electroacoustic transducer element, i.e. a transducer film electrode 20 made of piezoelectric material such as ZnO is provided on one flat surface of a solid state acoustic field medium 21 such as a sapphire rod having a diameter of 7 mm and a length of 11.5 mm, in the opposite surface of the medium 21 is formed a cylindrical concave surface 22. The cylindrical concave surface 22 is optically polished and has a radius of 1.0 mm and an aperture half-angle of 60 degrees. On the cylindrical concave surface 22 is applied an anti-reflection coating 23 of a quarter wavelength. This coating 23 may be formed by vacuum-evaporation of chalcogenide glass. Therefore, acoustic plane waves are propagated in the medium 21 and are focused linearly by the cylindrical lens constructed by the cylindrical concave surface 22. The linearly focused acoustic beam is projected via a liquid state acoustic field medium 24 such as water upon a specimen 25.

FIGS. 5a and 5b are graphs showing acoustic field distributions at a focusing plane of the linearly focused beam. FIG. 5a shows the distribution in an X axis direction which is perpendicular to a longitudinal axis of the cylindrical surface 22 and a half-width is about one wavelength and FIG. 5b illustrates the distribution curve in a Y axis direction which is parallel with the longitudinal axis of the cylindrical concave surface 22. The acoustic beam is not substantially focused in the Y axis direction and thus has a width which is substantially equal to the length of the cylindrical concave surface 23. In this manner the acoustic beam is linearly focused along the X axis and not focused along the Y-axis. The acoustic beam thus linearly focused only in one direction is called here a line-focus acoustic beam.

Figure 6A:
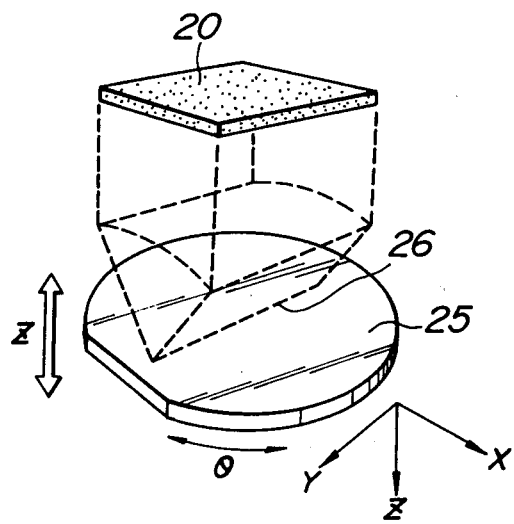
FIG. 6a is a perspective view depicting a relative arrangement of the acoustic transducer head and a specimen.

FIG. 6a is an explanatory schematic view showing a manner of detecting anisotropies of a specimen 25 about the Z-axis parallel to the axis of the line-focus acoustic beam 26 emitted from the transducer element 20. The line-focus acoustic beam 26 is projected via the liquid state acoustic field medium (not shown in FIG. 6a) upon the specimen 25. In the same manner as that of the known conically focused acoustic beam, the specimen 25 is moved in the Z axis direction to measure the above mentioned V(Z) curve. A relation between a period $\Delta Z$ of dips in the V(Z) curve and a velocity of leaky surface acoustic wave can be equally expressed by the above mentioned equations. The only difference is that according to the known conically focused acoustic beam the average value around the Z axis is measured, whereas according to the line-focus acoustic beam the phase velocity of leaky surface acoustic wave in one particular direction can be measured. In FIG. 6a, the propagating velocity in the X axis direction can be measured. Therefore, by rotating the specimen 25 about the Z axis, while the V(Z) curve measurement is repeatedly effected at respective rotational angles $\theta$, it is possible to measure the anisotropies of the specimen 25 around the Z axis as difference or variation in the velocity of the leaky surface-acoustic wave. That is to say, according to the invention the anisotropies of crystals can be represented in terms of the angle $\theta$ and the velocity.

Figure 6B:
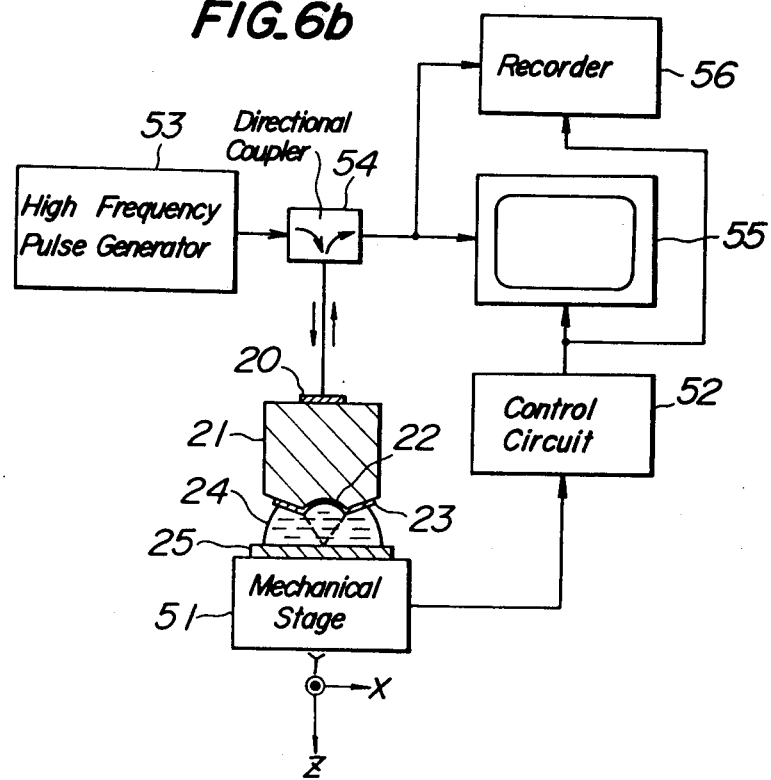
FIG. 6b is a schematic view showing a whole construction of the acoustic microscope according to the invention.
Figure 6C:
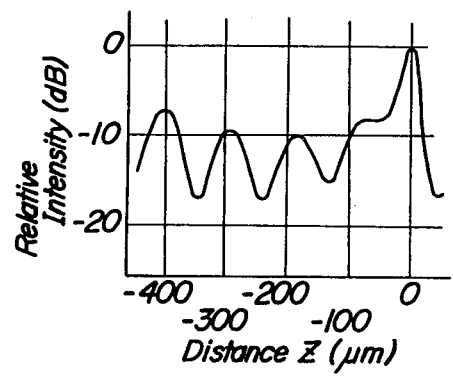
FIG. 6c is a graph of a measured V(Z) curve.

FIG. 6b is a schematic view showing an embodiment of the acoustic microscope according to the invention using the acoustic transducer head shown in FIGS. 4a and 4b. The acoustic transducer head is fixedly arranged above a mechaical stage 51 which is movable along three axes X, Y and Z and rotatable about the Z-axis under the control of a control circuit 52. A sample 25 is placed on the stage 51 at the focal point of the line-focus acoustic beam which is produced in response to a high frequency pulse generated from a pulse generator 53 and supplied to the transducer element 20 via a directional coupler 54. Then acoustic waves reflected from the specimen 25 are retranslated into an electrical signal by means of the acustic transducer head and the electrical signal thus obtained is displayed on a monitor 55 and is recorded by a recorder 56 such as digital wave memorizer. The position of the specimen 25 in the Z axis and the angle $\theta$ are detected by the control circuit 52 and the electrical output signal from the transducer head is supplied to the monitor 55 and the recorder 56 together with the Z position signal to display and record a V(Z) curve as shown in FIG. 6c. This V(Z) curve is obtained for Y-axis propagation ($\theta=30°$) of a leaky surface-acoustic wave on water/Z-cut sapphire boundary at an acoustic frequency of 202 MHz. From the V(Z) curve it is apparent that the periodicity appears remarkably and the period $\Delta Z$ of dips is measured as $\Delta Z=107.4$ $\mu$m. From the above equation (3), the velocity Vs of the leaky surface-acoustic wave in the Y direction is calculated to be 5,720 m/sec, while the longitudinal wave velocity $V_l$ in the water at 20° C. is assumed to 1,483 m/sec.

Figure 7:
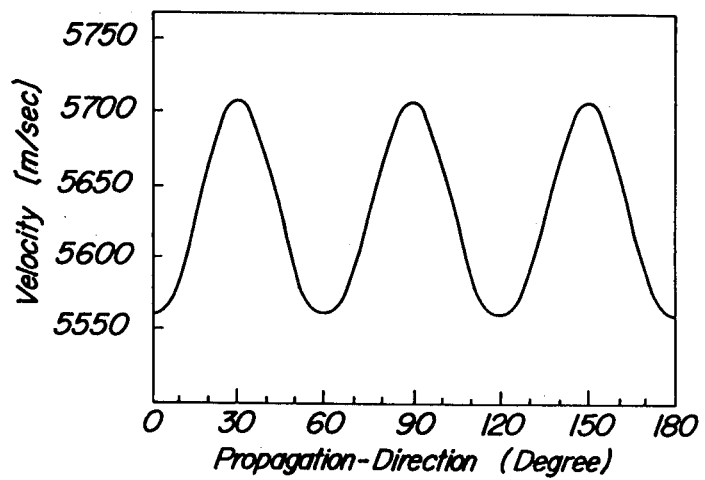
FIG. 7 is a graph showing a theoretical curve representing anisotropies about a Z axis of a Z-cut sapphire specimen.

Now an example of the measurements will be explained. In this example, use was made of a Z-cut sapphire (crystal system 3m) as the specimen 25. FIG. 7 is a graph showing a theoretical curve representing a dependence of the leaky surface-acoustic wave upon the propagating direction ($\theta$) due to the anisotropy of the sapphire plate about Z axis. As can be seen from the curve in FIG. 7, the anisotropy in all directions may be determined by effecting measurement within an angle range from $\theta=0°$ to $\theta=30°$.

The following table 1 shows measured and theoretical velocities and differences therebetween within the range of $0° \leq \theta \leq 30°$. In this example, the solid state acoustic field medium 21 was formed by a sapphire rod, water was used as the liquid state acoustic field medium 24, and the acoustic wave of 202 MHz was utilized.

TABLE 1

| Propagation Direction $\theta$ (degree) | Velocity (m/sec) Measured value Vm | Velocity (m/sec) Theoretical value Vc | Difference (%) $\frac{Vm - Vc}{Vc} \times 100$ |
|---|---|---|---|
| 0 | 5519 | 5560 | −0.74 |
| 5 | 5535 | 5568 | −0.59 |
| 10 | 5545 | 5593 | −0.86 |
| 15 | 5599 | 5629 | −0.53 |
| 20 | 5629 | 5668 | −0.69 |
| 25 | 5665 | 5699 | −0.60 |
| 30 | 5720 | 5711 | +0.16 |

It should be noted that the present invention is not limited to the embodiment explained above, but many modifications and alterations may be conceived by those skilled in the art within the scope of the invention. For instance, in the above embodiment, the acoustic transducer head emits a signal line-focus acoustic beam and thus, in order to investigate anisotropies of materials in greater detail, the measurement of V(Z) curve must be repeated at a large number of directions $\theta$. Therefore, the measurement is very cumbersome and requires time consuming work. In order to obviate such an inconvenience the acoustic transducer head may be constructed to emit a plurality of line-focus acoustic beams linearly focused in different directions. FIGS. 8a to 8e are diagrammatic plan views illustrating various embodiments of the acoustic transducer head according to the invention. FIG. 8a shows an embodiment similar to the embodiment shown in FIGS. 4a and 4b for producing the single line-focus acoustic beam. In this embodiment, a single transducer element 20 is applied on a flat end surface of the solid state acoustic field medium 21 and the corresponding acoustic lens having the cylindrical concave surface is formed in the opposite surface of the medium 21. It should be noted that the transducer element 20 and the corresponding cylindrical concave surface are formed to extend in the same direction. In an embodiment shown in FIG. 8b, two transducer elements 29a, 29b are provided on a flat end surface of a solid state acoustic field medium 28 and two corresponding cylindrical concave surfaces are formed in the opposite end surface. Since the transducer elements 29a and 29b are arranged perpendicularly to each other, the longitudinal axes of cylindrical concave surfaces are also made at right angles with each other. FIG. 8c shows a modified embodiment of the transducer head in FIG. 8b. In this modified embodiment, the transducer elements 29a and 29b and thus the corresponding cylindrical concave surfaces are arranged at an angle of about 30°. In an embodiment illustrated in FIG. 8d, three transducer elements 29a to 29c are arranged in such a manner that each of the elements are placed on respective sides of a regular triangle. In the embodiment shown in FIG. 8e, five transducer elements 29a to 29e are arranged on respective sides of a regular pentagon. It is matter of course that in the embodiments in FIGS. 8d and 8e, corresponding cylindrical concave surfaces are formed in the opposite end surface in such a manner that they are arranged on the corresponding regular triangle and pentagon, respectively. By utilizing the transducer heads illustrated in FIGS. 8b to 8e the V(Z) curves for different directions may be obtained substantially simultaneously with the aid of electronic switching means and thus the propagation velocities in different directions may be measured simultaneously. Then the specimen is rotated by a predetermined angle and the above mentioned measurement is repeated. In this manner, the anisotropies of materials may be measured and detected within a shorter time as compared with the above explained embodiment in which only the single line-focus acoustic beam is used.

Further, in the embodiments so far explained, the line-focus acoustic beam is formed by the acoustic lens, but it may be produced by means of other constructions. In an embodiment shown in FIG. 9a, an acoustic transducer element 31 made of piezoelectric material is directly applied onto a cylindrical concave surface of a block 30 made of metal or other solid material. In embodiments illustrated in FIGS. 9b and 9c, acoustic transducer elements 31 are applied on inner and outer cylindrical concave or convex surfaces, respectively of a substantially semicylindrical body 32. By means of such acoustic transducer head it is also possible to form the line-focus acoustic beam. Furthermore, the line-focus acoustic beam may also be obtained by an acoustic transducer head of phase arrangement type or of Fresnel zone plate type. Moreover, it should be noted that the acoustic microscope according to the present invention may be also used for investigating isotropic materials.

As explained above in detail, according to the acoustic microscope utilizing the line-focus acoustic beam of the present invention, anisotropies of crystals and the velocity of the leaky surface-acoustic wave propagating in any direction on any crystal cut surface can be measured in an easy and accurate manner.

What is claimed is:

1. An acoustic microscope for detecting acoustic properties of a specimen comprising:
    an acoustic transducer head for propagating an acoustic beam toward a specimen and which is linearly focussed in a direction perpendicular to the direction of propagation of the acoustic beam;
    means for moving the acoustic transducer head relative to a specimen in the direction of propagation of the acoustic beam; and
    means for rotating the acoustic transducer head relative to a specimen about an axis which is parallel with the direction of propagation of the acoustic beam.

2. An acoustic microscope according to claim 1, wherein said axis of rotation is made coincident with the direction of propagation of the acoustic beam.

3. An acoustic microscope according to claim 2, wherein said moving and rotating means comprise a mechanical stage which is movable in the direction of propagation of the acoustic beam and rotatable about the parallel axis, while said acoustic transducer head is fixed.

4. An acoustic microscope according to claim 1, wherein said acoustic transducer head comprises a solid state acoustic field medium having a flat end surface and at least one cylindrical concave surface formed in the opposite end surface, and at least one electroacoustic transducer element applied on said flat end surface of the solid state acoustic field medium.

5. An acoustic microscope according to claim 4, wherein said acoustic transducer head is so constructed that a half-width of the acoustic beam as viewed in said one direction is substantially equal to one wavelength of the acoustic beam.

6. An acoustic microscope according to claim 4, wherein an anti-reflection coating is applied onto said opposite end surface of the solid state acoustic field medium in which surface said cylindrical concave surface is formed.

7. An acoustic microscope according to claims 4, 5 or 6, wherein said solid state acoustic field medium is formed by a Z-cut sapphire rod.

8. An acoustic microscope according to claim 7, wherein said electroacoustic transducer element is formed by a ZnO film.

9. An acoustic microscope according to claim 4, wherein a plurality of the acoustic transducer elements are arranged on the flat end surface of the solid state acoustic field medium in such a manner that they make an angle unequal to zero relative to each other and the same number of the cylindrical concave surfaces as that of the transducer elements are formed in the opposite end surface of the solid state acoustic field medium in such a manner that each of them is aligned with the corresponding transducer element.

10. An acoustic microscope according to claim 1, wherein said acoustic transducer head comprises an acoustic transducer element which is applied on a cylindrical concave surface of a substrate.

11. An acoustic microscope according to claim 10, wherein said substrate is made of a semicylindrical body.

12. An acoustic microscope according to claim 1, wherein said acoustic transducer head comprises an acoustic transducer element applied on a cylindrical convex surface of a substrate made of acoustic field material.

13. An acoustic microscope according to claim 12, wherein said substrate is formed by a semicylindrical body.

14. An acoustic microscope for detecting acoustic properties of a specimen comprising:
    an acoustic transducer head for propagating an acoustic beam toward a specimen and which is linearly focussed in a direction perpendicular to the direction of propagation;
    said acoustic transducer head comprising a solid state acoustic field medium having a flat end surface and an opposite surface, a plurality of electroacoustic transducer elements arranged on said flat end surface in such a manner as to form angles relative to one another which do not equal zero, and a plurality of cylindrical concave surfaces equal in number to the number of said plurality of transducer elements and formed in said opposite surface in such a manner that each transducer element is aligned with a respective one of said concave surfaces.

* * * * *